(12) United States Patent
Fulton, III

(10) Patent No.: US 6,852,097 B1
(45) Date of Patent: Feb. 8, 2005

(54) MECHANICALLY ACTIVE INFUSION CATHETER

(76) Inventor: Richard E. Fulton, III, 1556 Wellington Ave., Grand Junction, CO (US) 81501

( * ) Notice: Subject to any disclaimer, the term of this patent is extended or adjusted under 35 U.S.C. 154(b) by 0 days.

(21) Appl. No.: 09/599,987

(22) Filed: Jun. 23, 2000

Related U.S. Application Data

(60) Provisional application No. 60/140,886, filed on Jun. 24, 1999.

(51) Int. Cl.$^7$ .......................... A61D 1/02; A61M 29/00; A61M 5/32
(52) U.S. Cl. ........................ 604/266; 606/159; 606/200
(58) Field of Search ................................. 606/191–200, 606/1, 159, 169, 170, 171, 180; 604/22, 266–269

(56) References Cited

U.S. PATENT DOCUMENTS

| | | | | |
|---|---|---|---|---|
| 3,996,938 A | | 12/1976 | Clark, III .................... 128/348 |
| 4,445,509 A | * | 5/1984 | Auth .......................... 606/159 |
| 4,747,406 A | | 5/1988 | Nash .......................... 128/305 |
| 4,923,462 A | | 5/1990 | Stevens ...................... 606/159 |
| 4,968,306 A | | 11/1990 | Huss et al. .................. 604/264 |
| 5,041,124 A | * | 8/1991 | Kensey et al. .............. 606/170 |
| 5,197,946 A | | 3/1993 | Tachibana .................... 602/22 |
| 5,250,034 A | | 10/1993 | Appling et al. ............. 604/164 |
| 5,267,979 A | | 12/1993 | Appling et al. ............. 604/247 |
| 5,279,546 A | * | 1/1994 | Mische et al. ................ 604/22 |
| 5,362,309 A | | 11/1994 | Carter ......................... 604/22 |
| 5,370,653 A | * | 12/1994 | Cragg ........................ 606/170 |
| 5,397,293 A | | 3/1995 | Alliger et al. ................. 601/2 |
| 5,425,723 A | | 6/1995 | Wang ......................... 604/280 |
| 5,443,443 A | * | 8/1995 | Shiber ......................... 604/22 |
| 5,569,275 A | * | 10/1996 | Kotula et al. ............... 606/159 |
| 5,624,396 A | | 4/1997 | McNamara et al. .......... 604/93 |
| 5,681,335 A | * | 10/1997 | Serra et al. ................. 606/159 |
| 5,702,413 A | * | 12/1997 | Lafontaine .................. 606/159 |
| 5,713,848 A | | 2/1998 | Dubrul et al. ................ 604/22 |
| 5,725,494 A | | 3/1998 | Brisken ........................ 604/22 |
| 5,766,191 A | | 6/1998 | Treretola .................... 606/159 |
| 5,782,797 A | | 7/1998 | Schweich et al. ............. 604/49 |
| 5,782,848 A | * | 7/1998 | Lennox ....................... 606/159 |
| 5,882,329 A | * | 3/1999 | Patterson et al. ............. 604/49 |
| 5,957,882 A | * | 9/1999 | Nita et al. ...................... 601/2 |
| 5,997,558 A | | 12/1999 | Nash .......................... 606/159 |
| 6,030,397 A | * | 2/2000 | Monetti et al. ............. 606/159 |
| 6,063,069 A | * | 5/2000 | Cragg et al. .................. 604/22 |

* cited by examiner

*Primary Examiner*—Larry I. Schwartz
*Assistant Examiner*—C. Lynne Anderson
(74) *Attorney, Agent, or Firm*—Sheridan Ross P.C.

(57) ABSTRACT

A device and method to dissolve or eliminate blood clots from a patient relies upon a non-rapid moving mechanism to physically dissolve clots without damaging endothelium of the arteries and veins of a patient. In one embodiment, in addition to mechanical agitation of a clot, a thrombolytic agent is administered simultaneously with such agitation. Preferably, intermittent agitation is utilized over a prolonged period of time to effectuate clot removal.

17 Claims, 7 Drawing Sheets

MECHANICALLY ACTIVE INFUSION CATHETER

RELATED APPLICATION

This application claims priority from U.S. Provisional Patent Application No. 60/140,886 filed on Jun. 24, 1999.

FIELD OF THE INVENTION

The present invention relates to a device and method utilized within the medical field to dissolve or eliminate blood clots that may block arteries, veins, grafts, implants, stents, catheters, and other structures. In one embodiment, pharmacological and mechanical action is combined to achieve this result.

BACKGROUND OF THE INVENTION

The presence of thrombus, or blood clot, within arteries, veins, grafts, and vascular channels of the bodies is a challenge to many disciplines of medicine. If the thrombus develops acutely, it may create a medical emergency. Even if the thrombus develops gradually, conservative medical management with drugs is frequently less than satisfactory. Surgical intervention is an alternative, although a costly, and, at times, an ineffective one in many cases. Catheter directed thrombolysis is effective, but time consuming and very costly, because of the expense of the drug and the intensive care needed to monitor this therapy. A successful catheter infusion thrombolysis may take 36 to 48 hours to achieve complete thrombolysis.

Mechanical thrombolytic devices have been developed which are quick and effective in dialysis grafts, mainly because of the nature of such fresh unorganized clots presented in such situations, but such devices are not effective in removing most of the thrombus in arteries and veins of the body. Many of these mechanical devices have the potential to damage the endothelium of the arteries and veins, as well. The endothelium is a fragile covering of the inside of arteries and vessels, and is easily damaged with mechanical forces. This may cause a cascade of events resulting in thrombosis, restenosis, accelerated atherosclerosis, valvular dysfunction, platelet aggregation, late thrombus formation, and other untoward events. By damaging the endothelium during percutaneous thrombolysis, long term patency of the vessel is compromised.

Many mechanical thrombolytic devices have been developed to hasten the process of non-surgically eliminating clot from blood vessels, but in most cases, they fail to remove all of the clot. This necessitates an additional procedure of protracted infusion of a thrombolytic drug, which is the procedure the mechanical thrombolytic devices were designed to replace.

Mechanical devices exist that also deliver a drug to aid in the dissolution of thrombus, but are utilized and then removed, usually in 20–40 minutes. Such methods and devices do provide mechanical action over a protracted period of time while the drug is being infused. As a result, there is invariably thrombus remaining at the termination of the procedure, necessitating the infusion of a thrombolytic drug through a different catheter for a protracted period of time to eliminate the remaining clot. This proves costly as more resources in the form of personnel and the expensive drugs are consumed.

The prior art mechanical thrombolytic devices and the prior art combination mechanical-pharmacologic devices are therefore designed to be operated mechanically for short periods of time, usually 20–40 minutes total, and at very high speeds or frequencies. Prior art devices are designed to act in short, intense bursts and involve rotating baskets and brushes, propellers, water jet, Venturi effect, vibrational, and other mechanical methods. The mechanical action is often effective in debulking, or lessening, the clot burden, but rarely effective in removing or dissolving all of the clot. Part of the reason is that a clot adherent to the wall of the vessel is not affected by these mechanical devices. The use of these devices to perform the incomplete mechanical thrombolysis necessitates a procedure which demands the attention and the time of a physician, a nurse, and several technologists in an interventional suite, catheterization lab, or operating room.

The prior art devices are also expensive, typically costing $500–700 or more. This tremendous expenditure of time, effort, and supplies is usually not rewarded with complete success, creating a need to place another expensive infusion catheter within the clot, transferring the patient to an intensive observation area, and infusing thrombolytic drug(s) for a protracted period. The patient is then returned to the interventional suite many hours later, and most often, the action of the thrombolytic drug has resulted in complete thrombolysis with no residual clot.

The net consequence is that a lot of time, energy, personnel, and money are expended with the use of prior art mechanical and pharmaco-mechanical devices, with incomplete results, necessitating the use of a relatively long infusion to effect complete thrombolysis. Therefore, the use of the prior art devices to dissolve a clot during the course of a procedural intervention is unsatisfactory, and an unnecessary consumption of resources. Moreover, the design and speeds at which such devices operate risk significant injury to a patient.

The existing mechanical and pharmacomechanical devices also suffer from a design that limits the thrombolytic action to an area near the tip of the catheter. This is true of the rotating baskets, propeller type devices, rotating brushes, water jet, ultrasonic, sub-sonic, vortex, and other mechanical thrombolytic devices. Many of these can be activated for only short periods of time, i.e., seconds or minutes, lest they overheat or cause hemolysis or blood loss. There is a real potential for many of them to damage the endothelium, or lining of the blood vessels, if used for more than a few seconds at a time. Moreover, the pharmacomechanical devices have apertures for injecting the thrombolytic drug near the tip of the catheter as well. While these designs may be satisfactory for a short segment occlusion of 10 cm. or so, frequently the occlusion because of thrombus is much longer. Such prior art devices must be advanced and retracted within the lumen of the occluded vessel to "treat" one segment of the vessel at a time, usually resulting in incomplete and ineffective treatment of the entire occluded segment, thus requiring the need for the patient to undergo a prolonged infusion of the thrombolytic drug with the attendant increase in costs. Typically, the thrombus within the deep venous system of the leg needing interventional therapy extends from the calf veins to the inferior vena cava, a length of 40–60 cm. Femoral-popliteal arterial grafts are 30 cm. or so.

There are many prior art devices for the treatment of thrombus or blood clot within the arteries and veins of the body, as the occurrence of blood clots is a common and serious medical condition. The trend toward lesser invasive procedures has benefited patients in improved outcomes, less morbidity, and without the need for surgery. There are many prior art catheters designed for infusion of lytic agents, such as urokinase and tissue plasminogen activator substance (tPA). Representative of these are U.S. Pat. Nos. 4,968,306, 5,250,034, 5,267,979, 5,624,396, 5,782,797, and 5,425,723. The process of infusion and dissolution of the thrombus is a lengthy one, taking 24 to 48 hours frequently. The lytic agent bathes the thrombus and pharmacologically dissolves the thrombus over time. Such methods necessitate the use of a large amount of expensive drug or lytic agent and overnight monitoring in a critical care unit. The process may cost upwards of $20–30,000.

Purely mechanical thrombolytic devices were developed as an alternative to infusion thrombolysis. These devices attempt to dissolve the clot in a relative short procedure, usually less than an hour. Representative of these are U.S. Pat. Nos. 4,747,406, 4,923,462, 5,569,275, 5,397,293, 5,766,191, and 5,997,558. While they may be effective in removing a large amount of the thrombus in a relatively short period of time, there is usually incomplete thrombus removal necessitating further infusion of lytic agents to dissolve the residual thrombus. Moreover, they remove enough of the clot so that partial flow may be reestablished within the vessel, causing the lytic agent to be washed out of the clot containing vessel as it is being infused.

Combination devices which utilize mechanical thrombus disruption and pharmacological agent infusion are represented by U.S. Pat. Nos. 5,279,546, 5,197,946, 5,362,309, 5,279,456, 5,725,494, and 5,713,848. These combination devices are an improvement, in that they attempt to utilize a lytic agent and mechanical motion of various types to disrupt the clot. They however, are time inefficient and the action of the lytic agent usually takes hours to achieve complete thrombolysis. All of the prior art combination devices are used within the confines of a procedural intervention that takes less than an hour and would damage the endothelium if used for more protracted periods of time. Many would overheat or fail, as the mechanical motion demands high frequency vibrations or rotation. Even Dubrul, U.S. Pat. No. 5,731,3848 at the lowest frequency of one vibration/second, would damage the endothelium if activated for several hours.

There is a dichotomy in the design of all of these prior art thrombolytic catheters. The pure infusion catheters only passively bathe the clot and have no method of increasing the surface area of the clot to be dissolved. They demand very protracted infusions to clear the clot. The purely mechanical devices diminish clot burden, at a cost of time, materials, and personnel, but frequently leave significant residual clot requiring a prolonged infusion. The combination pharmaco-mechanical devices attempt to fragment the clot and deliver the lytic agent simultaneously, but are only able to be mechanically active for short periods of time, usually not enough time for the lytic agent to dissolve the clot.

Therefore, there is a need for a device which provides a mechanical action to increase the surface area of the clot for efficacious dissolution by the lytic agent, provides this mechanical action for a prolonged period of time while the lytic agent is acting, provides a mechanical action which is not harmful to the endothelium of the vessel, and is time efficient for the operator and the patient.

SUMMARY OF THE INVENTION

The device of the present invention differs from all of the prior art devices in that it provides a mechanical means of gradually disrupting the clot as the lytic agent is acting, usually over a few hours. It overcomes the problems of potential mechanical failure or endothelial damage which would occur should the other pharmaco-mechanical devices be used over a period of several hours. It overcomes the problem of trying to dissolve some of the clot with an expensive mechanical device and all of the attendant problems listed above. It overcomes the problem of extremely protracted passive infusion thrombolysis.

The device of the present invention obviates the need for the above described prior art procedural interventions and use of prior art devices by providing a device which is simply placed into the clot or thrombus, and the intermittent mechanical action and continuous or intermittent infusion of lytic agent occurs, preferably, after the patient has been transferred to the observation area. As more completely described below, the present invention saves the step of intense mechanical intervention, saving costs in time, personnel, and materials. The present invention also lessens the time and the amount of drug needed for thrombolysis when compared to standard non-mechanical infusion thrombolysis.

The present invention satisfies the long-felt, but unsolved need for a pharmacomechanical thrombolytic device that will be effective over lengths of vascular veins and arteries and which can be utilized continuously, or intermittently, over several hours to allow the thrombolytic drug to be completely dissolve the thrombus. The mechanical component of the present invention disrupts the clot and provides more surface area for the thrombolytic drug to act upon.

Accordingly, it is one object of the current invention to solve the problems experienced in using prior art devices and methods by providing a device that is mechanically active over a substantial length of the catheter while allowing the thrombolytic drug to be infused or injected over the same substantial length of the catheter. It is also an object of the present invention to permit synergy of the mechanical and pharmacologic actions over a prolonged period of time, i.e., up to several hours, without damaging the endothelium of the vessel containing the clot. It is an object of the current invention to combine two elements: 1) pharmacomechanical device having a working length sufficient to span most or all of the length of a clot, and 2) provision of means to allow the pharmacomechanical action to occur over a protracted time period. Another object is to create cost efficiencies by diminishing the time and amount of drug to realize thrombolysis.

DETAILED DESCRIPTION OF THE PREFERRED EMBODIMENT

The current invention may take any one of several forms, but the preferred embodiment is that of a catheter (hereinafter meant to generally refer to any guide wire, infusible wire, or similar conduit) which is capable of delivering a thrombolytic agent and creating mechanical disruption of the clot while the thrombolytic agent is being delivered. The mechanical motion or mechanical action can take one of several forms which are described below. The mechanical motion is intermittent and more gentle than prior art devices to prevent hemolysis and endothelial damage. The mechanical motion is slower (e.g., less than 200 rpm, more preferably less than about 600 rpm, and most preferably less than about 55 rpm) than prior art devices and the mechanical motion occurs intermittently, at preselected intervals. The mechanical action is therefore of a non-rapid type which can be adjusted for different slow speeds. As an example, the mechanical action may be activated for two seconds and then inactive for five minutes, activated for two seconds and then inactive for five minutes, and so on until thrombolysis occurs. Various factors influence the choice of the parameters of speed of action (rpm's or cycles/sec), time of activation, time of inactivation, total treatment time (time of activation plus time of inactivation), repetition time, as well as the infusion rate of the lytic agent. These factors include the location of the clot, as more aggressive thrombolysis with rapid speed of action, longer activation times and shorter inactivation times can be achieved within grafts as there is no concern of damaging the endothelium. However if the thrombus is within a native artery or vein, the speed would be slower, time of activation shorter, and time of inactivation longer to keep from damaging the endothelium. The age of the clot or thrombus is a critical determinant in the total treatment time, as fresh or subacute clot (hours to a few days) will dissolve more quickly and easier than a clot which has been present for longer than 10 days or so. The size of the clot also is a determinant in the choices. A less aggressive (shorter activation times) and shorter total treatment time is chosen for a relatively small clot of recent vintage. The parameters for the lytic therapy infusion may be varied as well depending on the site, age of thrombus, size of thrombus, etc. Therefore, the preferred embodiment and preferred parameters may be site specific.

Figure 1:
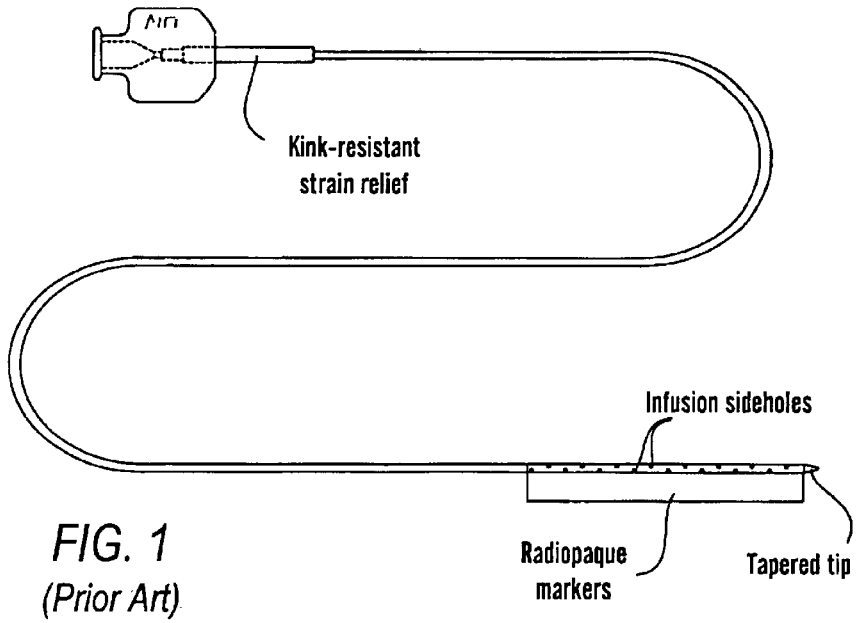
FIG. 1 is a depiction of a prior art thrombolytic catheter.
Figure 2:
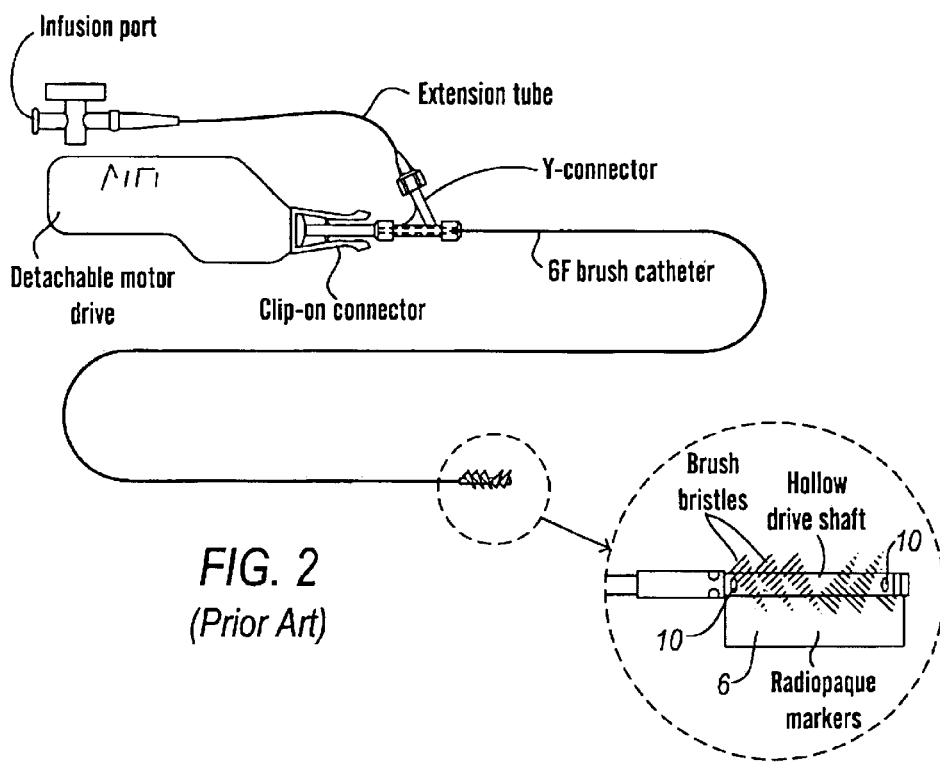
FIG. 2 is a depiction of a prior art pharmacomechanical thromblytic device. The brushes 6 near the tip provide the mechanical disruptive action and one or two side holes 10 immediately proximal to the brushes 6 allow infusion of the thrombolytic drug.
Figure 3:
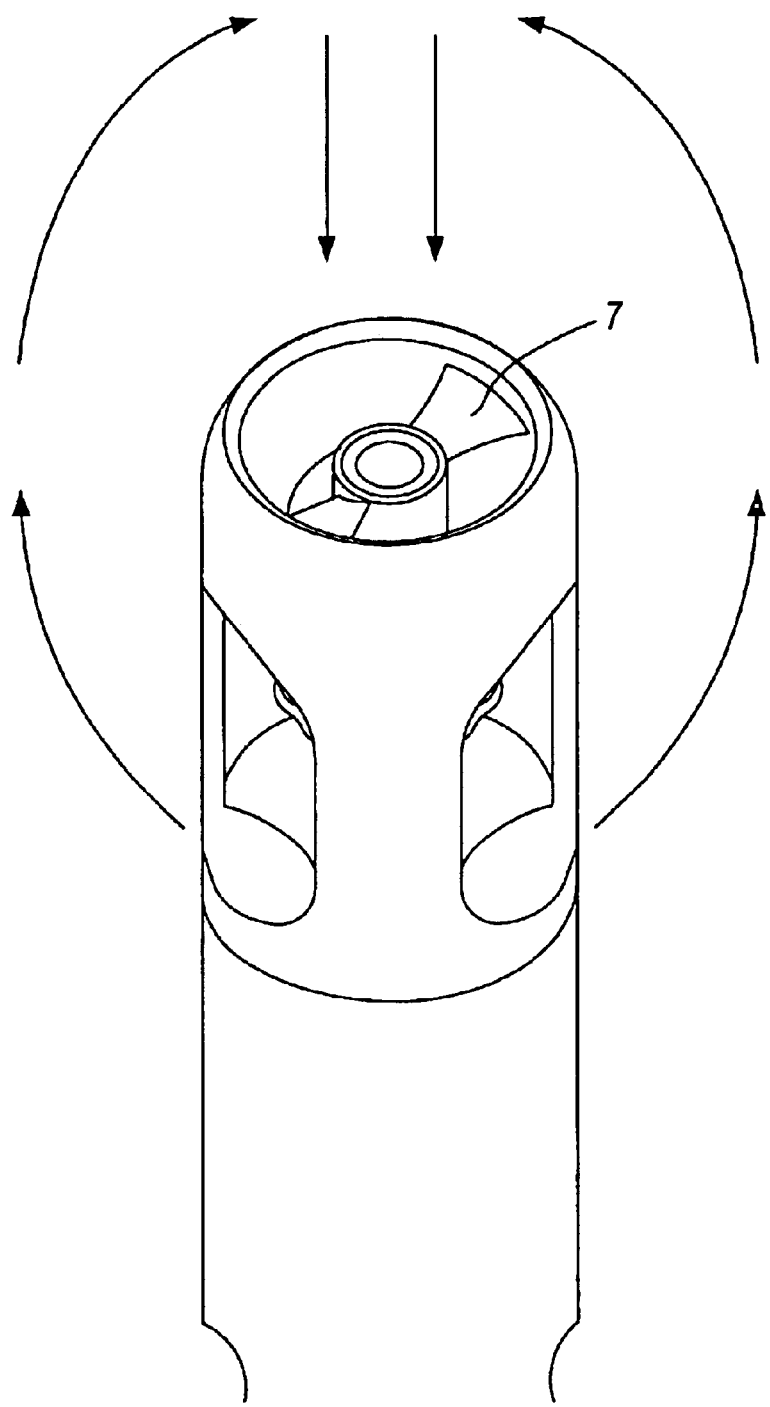
FIG. 3 is a depiction of the distal tip of a prior art mechanical thrombolytic device showing a propeller blade 7 used to create a vortex which disrupts a clot.
Figure 4:
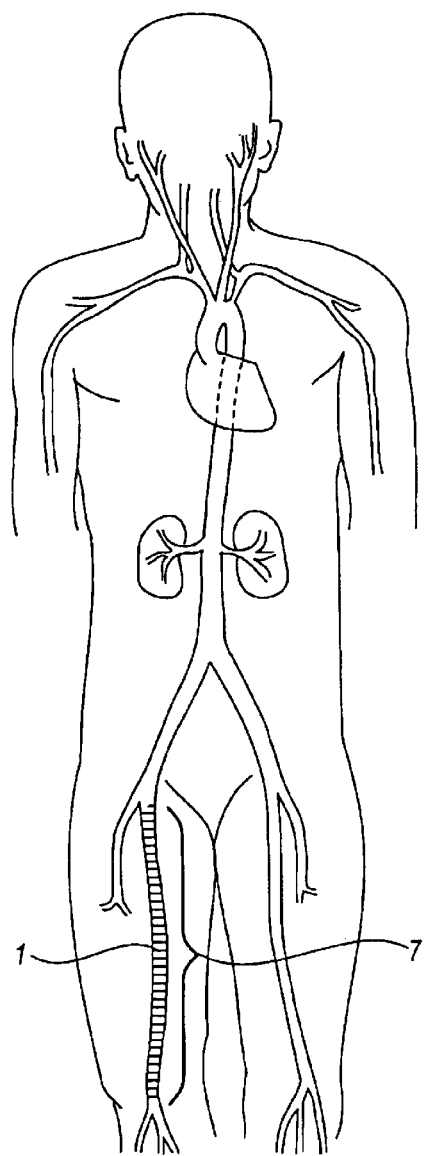
FIG. 4 demonstrates the major arteries of the body, with the right superficial femoral artery 2 representing thrombus 1 prior to catheter directed thrombolysis.
Figure 5:
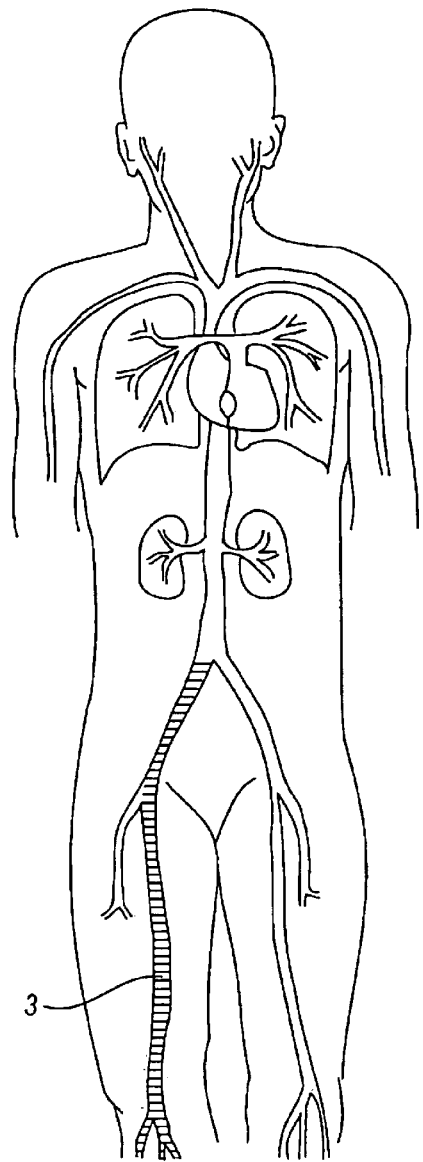
FIG. 5 demonstrates the major veins of the body, with right iliofemoral venous 3 thrombosis prior to catheter directed thrombolysis illustrated.
Figures 6, 7:
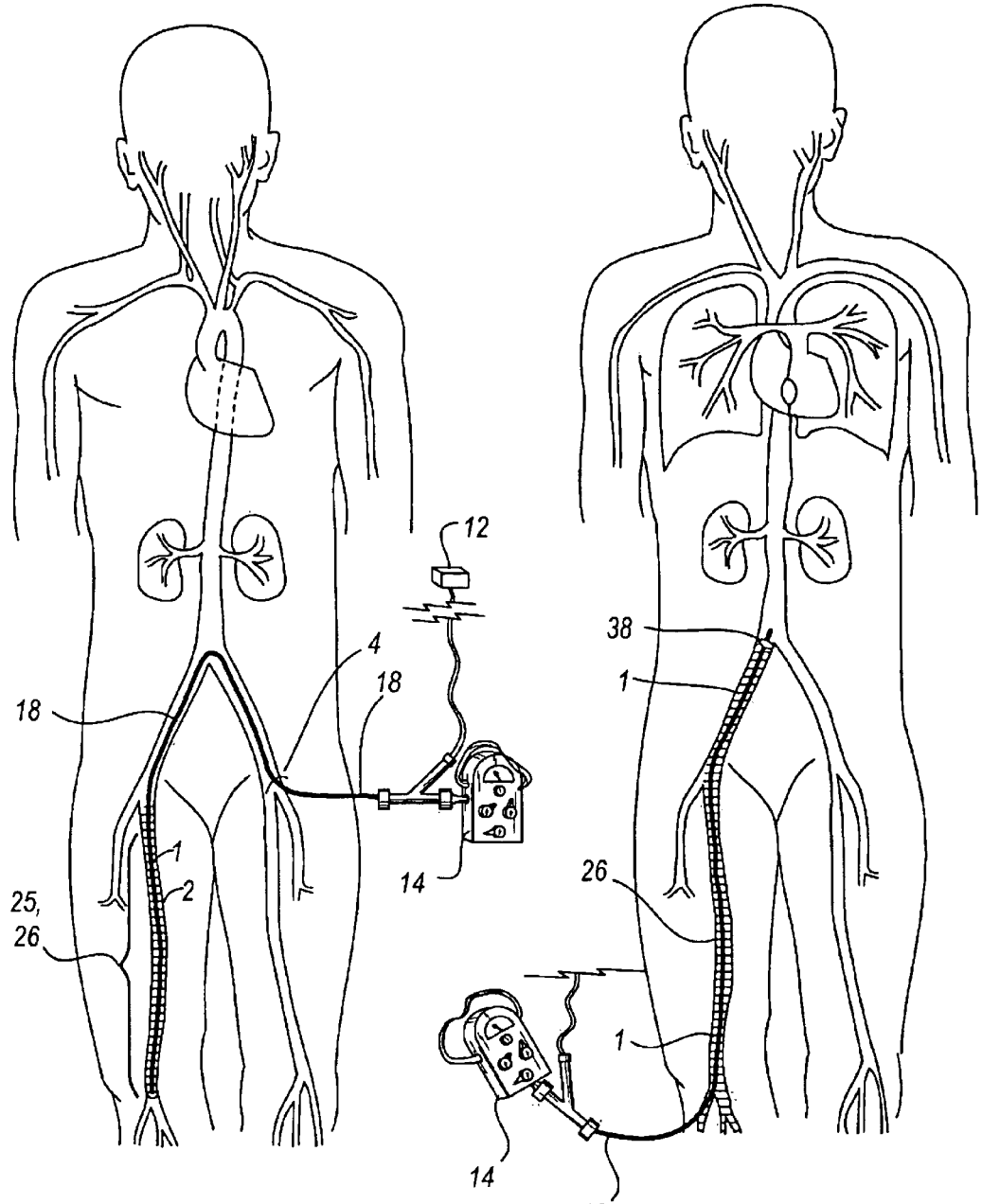
FIG. 6 represents the catheter device 18 of the present invention entering the left common femoral artery 4 directed into and through the thrombosed artery 2 in FIG. 4, the mechanically active segment and the infusion segment 26 span the entire length of the clot 1.
FIG. 7 represents the catheter device 18 of the present invention entering the right popliteal vein and the pharmacomechanical active segment 26 spanning the entire length of the clot 1.

Generally, the device 18 of the present invention (FIG. 6) comprises an infusion pump 12 which infuses the lytic agent at a continuous selected rate. The device 18 of the present invention is simply placed into the clot 1 and the patient sent to an observation area where the lytic agent and mechanical action occur. The interventionalist, team, and suite are free to perform other cases while the intermittent mechanical action and lytic agent infusion are being achieved.

In one alternative embodiment, the lytic agent is infused intermittently (e.g., over a period of minutes, such as every 5–15 minutes, or even longer time periods, such as every ½ hour, etc.). The mechanical action may be selected from a range of 0.1–600 rpms with activation times of about 0.1 second to about 60 seconds, and inactivation times of 5 seconds to 20 minutes. Typically, the parameters chosen for a relatively fresh long segment lower extremity venous thrombus are: a) continuous infusion of the lytic agent, b) mechanical action speed of about 55 rpm's, c) activation time of at least about 3 seconds, and d) inactivation time of 3 minutes. Preferred parameters for a long segment arterial occlusion are: a) continuous infusion of the lytic agent, b) mechanical action speed of action speed of about 30 rpms (0.5 cycle/sec), c) activation time of at least about 2 seconds, and d) inactivation time of at least about 3 minutes. A preferred parameter setting for a graft is: a) continuous infusion of the lytic agent, b) mechanical action speed of about 300 rpms, c) activation time of about about 5 seconds, and d) inactivation time of about 1.5 minutes. Of course, as discussed above, the clinical setting and patient condition may require alternative parameters, and the above are suggested only as examples.

Intermittent action provides for relatively long periods of no mechanical action in which the endothelium is not contacted, scraped, or damaged. The slower action of 30–55 rpm's (less than 1 cycle/second) and the short activation times of 2–3 seconds prevents abrasion and damage of the endothelium as well. It is the intent of the current invention to provide a time of inactivity which is at least as great, and preferably substantially greater, than the time of activity of the device. This serves to protect the endothelium, but also creates an environment for accelerated thrombolysis by the lytic agent. The slower speed of the mechanical action along with the very short activation times with relatively long periods of inactivation allows the mechanical action to continue for at least several hours while the lytic agent is acting to dissolve the clot. As an example, if the total treatment time is three hours, and a mechanical action speed of 30 rpm's is used with an activation time of 2 seconds, and inactivation time of 3 minutes, a total of only 60 cycles of mechanical action would occur in the entire treatment. This will be sufficient to create the environment for accelerated thrombolysis, but not sufficient to cause endothelial damage.

The endpoint is resolution of the clot, which will vary from patient to patient, location to location, and depend on the age and size of the clot amongst other factors. Typically, however, a total treatment time of about one to three hours is anticipated to lyse fresh venous and arterial thrombus with the above techniques, although total treatment times of about 30 minutes to about 36 hours are generally anticipated. The slower, intermittent mechanical action of the device augments the action of the lytic agent by enhancing admixture of the lytic agent and clot, by creating more surface area within the clot, and by mechanical disruption of the clot, while avoiding damage to the endothelium.

Alternative embodiments include a catheter (preferably a single catheter) with just a means to create the mechanical action, without any means to treat the thrombus pharmacologically. Another embodiment allows the infusion of the thrombolytic agent after the mechanical portion is activated. Both the mechanical and the pharmacological delivery elements 25,26 (FIGS. 6, 7, 10, 11) preferably are effective over a substantial length of the catheter 18, rather than just concentrated at the tip, as is the case with prior art devices.

The mechanical element may be one of several types, i.e., ultrasonic, vibrational, rotational, bi-rotational, longitudinal motion, expansile, and the like. A suitable mechanical element may be a wire or a smooth wall catheter, have apertures 10 for the injection of the thrombolytic agent, or projections from the side of the device to better disrupt the thrombus (not shown.) A preferred embodiment uses wave like undulations or vibrations to disrupt the clot slowly while the pharmacological agent is being infused. Since the mechanical motion is intended to be used for some protracted period of time, it is advantageous for the mechanical motion to be one which does not promote hemolysis nor damages the endothelium. A slower motion rather than a rapid motion is therefore desirable.

In one embodiment (FIG. 10), a motor 14 that causes the catheter 18 to vibrate or undulate is attached to a wire 20 that is inserted within a lumen 28 of the catheter 18 or to the catheter 18 itself Braiding within the wall of the catheter 18 to enhance transmissions of the vibrations may be utilized, and this may obviate the need to insert a wire 20 within the catheter 18. A stiff segment 24 of the catheter 18 proximally is desirable, as the efficiency of transmitting the vibrations from the motor 14 to the mechanical element segment 26 is then enhanced. One may compare this stiffer or more rigid proximal segment 24 to a fly rod transferring energy to a fly line or the handle of a bullwhip causing the action of the whip. Again, it is the intent that a substantial length of the intravascular portion of the catheter is provided with the mechanical action.

A separate sheath component (22, FIG. 10) through which the device 18 is inserted may be used to keep the entirety of the device 18 from being mechanically active. In this case, the outer sheath 22 houses a proximal portion 24 of the device 18 and the mechanically active portion 26 of the device 18 extends distal to the tip of the outer sheath 22. In one embodiment, the catheter 18, at least in the mechanically active segment 26, contains only one lumen 28, although more than one lumen is feasible.

Another method to accomplish an effective mechanical motion (not shown) is to place two wires in a catheter wall so that they are disposed on opposite sides of the lumen. The wires are moveable within the catheter wall proximally and affixed at a point at which the mechanical motion is to begin. An alternating to and fro motion of the two wires causes the catheter to undulate distal to the fixation point. A motor 14 provides the desired motion of the two wires.

Still another method of effective mechanical motion involves a catheter having a spiral shape in the distal desired length. Such a catheter is straight proximally 24, but of a spiral configuration in the desired mechanical element segment 26. A motor 14 causes the catheter 18 to spin at a rather slow rate (approximately one to 300 times per minute). The proximal portion 24, because it is straight, does not have any substantial mechanical disruptive motion. The distal portion 26, because of the spiral configuration, spins in a corkscrew manner against the clot 1 or wall of the vessel, disrupting the clot.

Where the catheter includes a guide wire 20 to stiffen it, and where a lytic agent may be infused through side holes 10, the guide wire 20 may by spiral shaped as well. A guide wire (not shown) with a removable inner straight mandrel and an outer cylinder of shaped memory alloy may be utilized to create the spiral or corkscrew configuration. When the inner mandrel is within the outer sleeve or cylinder of the guide wire, the guide wire is stiff and more or less straight. When the inner core is removed the guide wire assumes a spiral configuration causing the infusion catheter over it to also assume a spiral or corkscrew configuration.

A variation of the above entails rotating the spiral catheter 18 one way and then the other, similar to an agitator in a washing machine. A motor 14 is provided to effect such motion. Yet another modification involves a serpentine or other shape to the catheter. Any motion can be employed with any different shape. Complex motions, such as a longitudinal wave like motion of the catheter combined with axial rotation, may be advantageous.

In another embodiment, an intermittent motion of the catheter is provided by a pump (not shown) that delivers lytic agent forcefully in programmable pulses. Such a pump is commercially available (AngioDynamics, Queensbury, N.Y.). It generates abrupt pulse waves which cause the lytic agent to be sprayed into the thrombus through side holes 10 in the catheter 18. Generally, the connecting tubes dissipate the motion caused when this abrupt and forceful pulse of medicine occurs. By more rigidly connecting the Pulse-Spray pump to the device of the current invention and preventing the dissipation of the pulse wave forces in the connecting tube, the pulse wave forces are transferred to the device of the current invention, causing it to move within the body. The connecting elements may be made of steel or any other rigid substance that is capable of transferring the forces from the Pulse-Spray machine to the catheter efficiently so that the catheter is mechanically active as described above. Since the frequency and duration of pulses are programmable on the pump, a separate motor to move the catheter will not be needed. Alternatively, a flexible catheter may be provided which is serpentine or spiral in shape. The pulse of the Pulse-Spray pump will straighten the catheter from its original shape, causing desired motion within the clot while the lytic agent is being dispersed.

An intermittent motion may be provided to any of the embodiments, i.e., so that the mechanical motion is activated every few seconds, every few minutes, or for any given time period. In fact, this is desirable to prevent damage to the vessel endothelium, but allows for enough clot disruption to enhance the action of the thrombolytic agent. The present invention is intended to provide a slow, intermittent motion over several hours to allow a lytic agent to work completely while not damaging the endothelium. Of course, the device may employ mechanical motion without the addition of a thrombolytic drug. Therefore, the current invention differs from prior art devices in many respects, including shape, length of mechanically active segment 26, the rapidity of the motion, the programmability of the motor drive 14, shorter periods of activity, longer periods of inactivity, the ratio of periods of inactivity to periods of activity, the number of total cycles of mechanical action during a treatment, as well as other features described herein.

In one embodiment (FIG. 10), a catheter 18 is constructed with multiple apertures (side holes, slits, or other openings) 10 through which a thrombolytic drug, when utilized, is injected or delivered. A separate pump 12 controls the rate and duration of drug administration. The apertures 10 are positioned throughout the mechanical motion segment 26 of the catheter, which may include much of the body of the catheter in addition to the area near the catheter tip. The apertures 10 preferably occupy about 20–60 cm. of the distal aspect of the catheter, rather than the typical distal 10 cm. of other prior art devices, although the apertures may occupy from 5–60 cm. of the distal aspect of the catheter.

The motor 14 which drives the mechanical portion 26 of the device 18 are typically different than those of the prior art, which are designed to be utilized for a short time during a procedure and are typically hand held devices with a finger activation, which rotate at very high rpm's. The motor 14 of the current invention may be programmable 15 to rotate at slower rates (about 0.1–600 rpms) over much longer periods of time (30 minutes-days.) In a preferred embodiment, the motor 14 may be programmed 15 to rotate, or have other mechanical action, at a mechanical action rate, or speed, of about 0.5 to 55 rpms and a total treatment time of about 30 minutes to 5 hours. The activation times may vary from about 0.1–60 seconds and the inactivation times may vary from about 5 sec to 20 minutes in the preferred embodiment. The program 15 may contain an intermittent mode in which there would be no motion provided by the catheter for specified periods of time. A motor controller 13, which is programmable 15, may be incorporated into the motor 14 or may be separate. The motor housing 14a is designed to accompany the patient to the ward or critical care unit so that it can be monitored while the pharmacomechanical thrombolysis proceeds. A battery and/or electrical connections are provided (not shown.)

Figure 8:
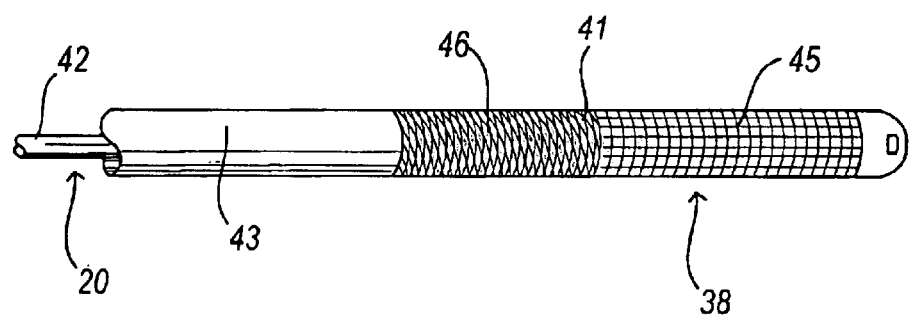
FIG. 8 demonstrates a deformable mesh braid 45 of an occluding element 38 in an undeployed, longitudinal, tubular orientation, and showing the inner core 42 and the outer surface 43 of the wire 20.
Figure 9:
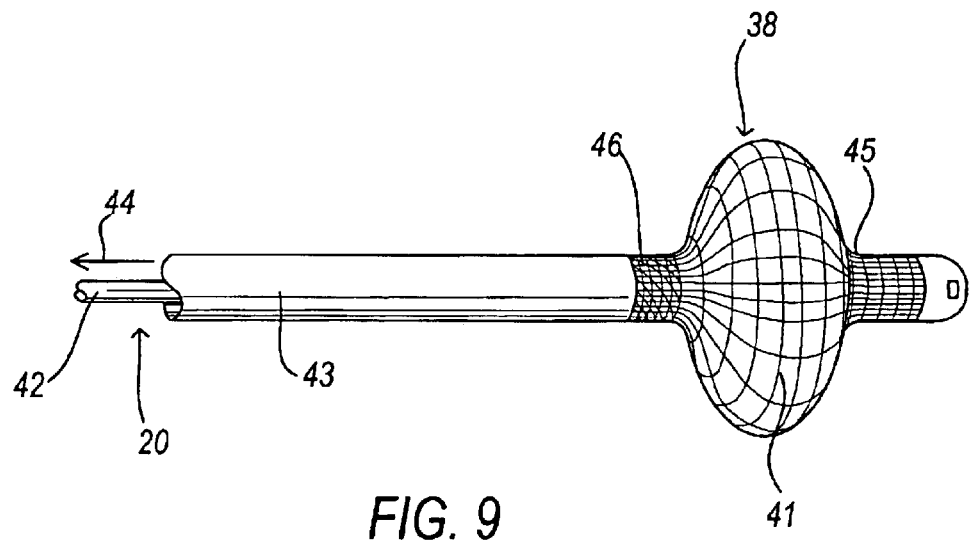
FIG. 9 demonstrates the occluding element 38 comprising mesh braid 45 in a deployed radially expanded state. The element 38 occludes the lumen of the vessel and prevents the thrombolytic drug from being washed away from the area of the thrombus. It should be noted that the outer 43 or inner core 42 of the wire 20 may be of varying stiffness, i.e., stiff proximally and limber distally, to facilitate the mechanical action of the device 18. Also the occluding element 38 may be used as a tensioner to facilitate the mechanical action, and as a clot dragger to remove residual thrombus.
Figure 10:
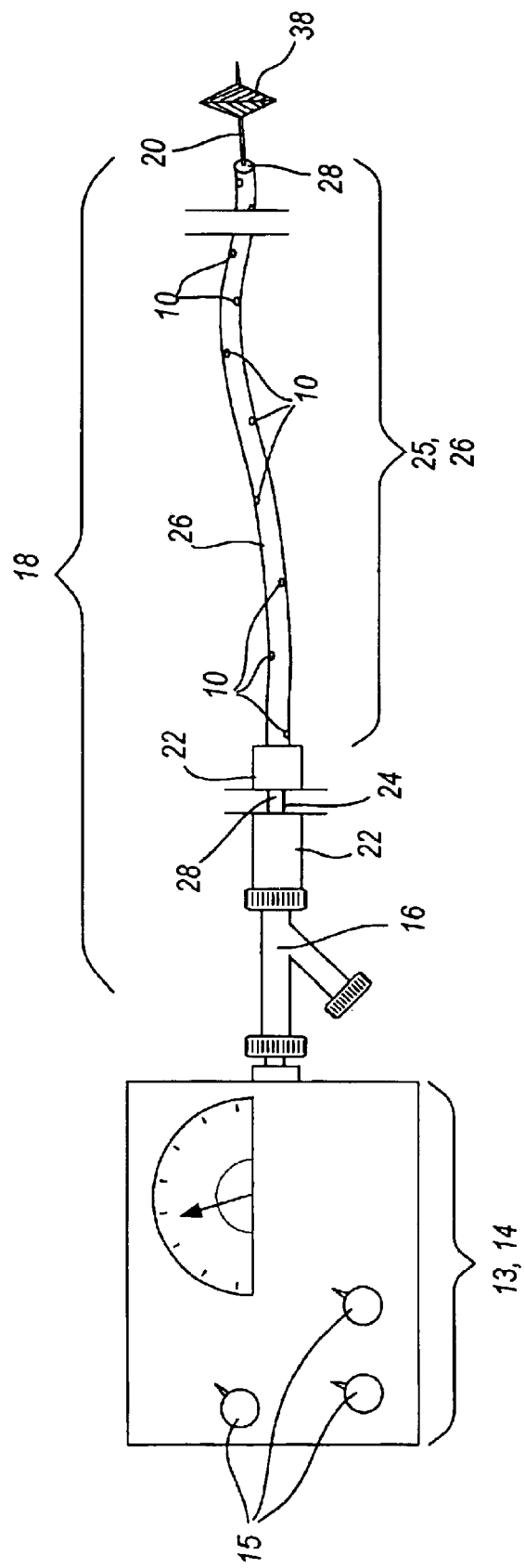
FIG. 10 is a representation of the device demonstrating, from left to right, the drive motor 14 with the controller 13 incorporated, a "Y" adapter 16 to receive the line from the drug infusion pump 12, the outer sheath 22 to prevent the proximal portion 24 of the catheter from being mechanically active, the mechanically active segment 26 of the device 18 containing infusion apertures 10, and the occluding element 38. The arrows indicate motion of the mechanically active segment 26. Preferably the mechanically active segment 26 of the device contains only one lumen 28 which will house the guide wire 20 of the occluding element 38 and allow the thrombolytic drug to be infused. The wall of the device may incorporate braided wires or other stiffening material to facilitate the mechanical action.
Figure 11:
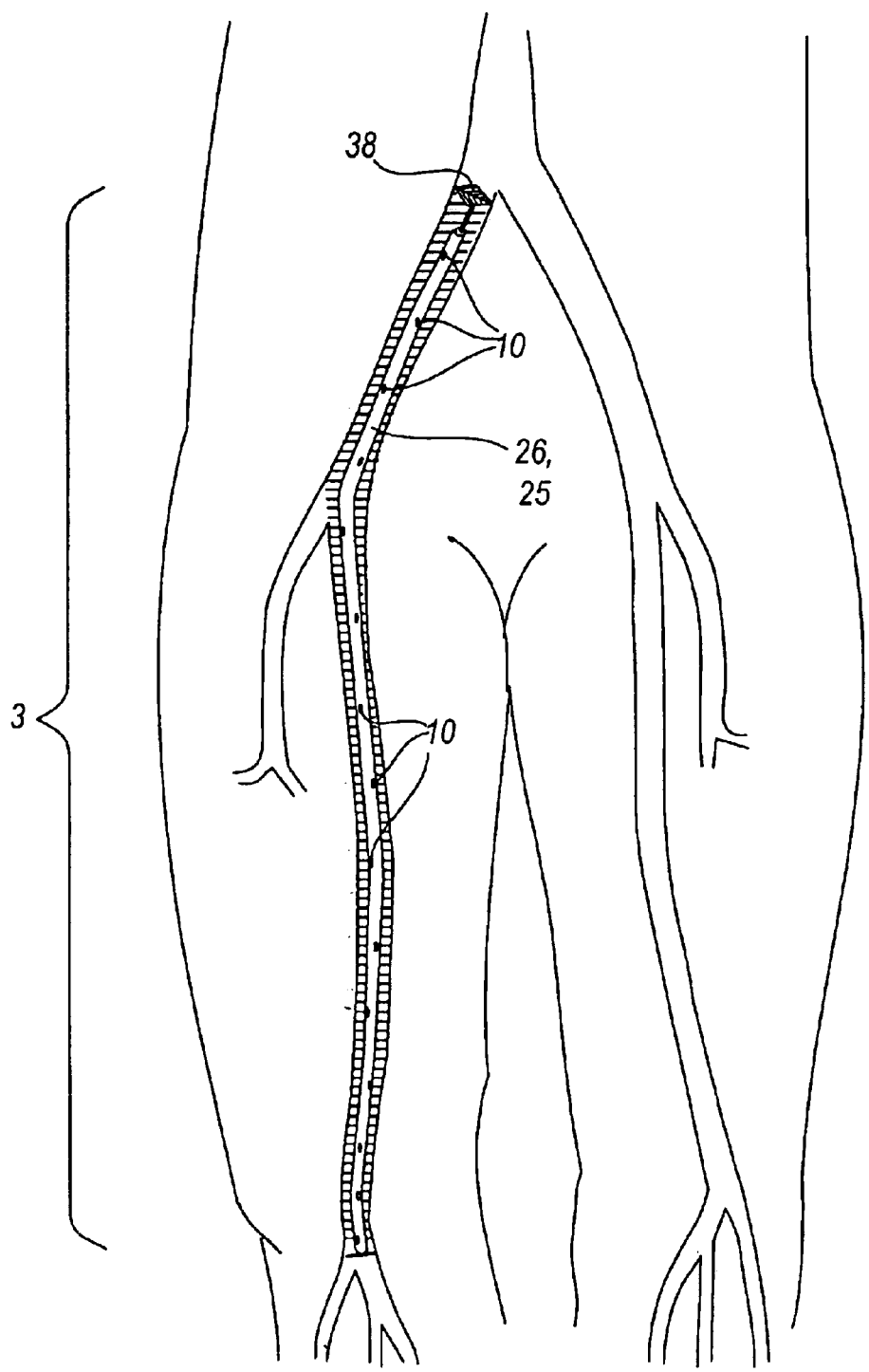
FIG. 11 illustrates the mechanically active segment 26 with the infusion apertures 10 present within the popliteal, femoral, and iliac veins 3 of a patient. The occluding element 38 is deployed.

Another aspect of the present invention (FIGS. 8, 9, 10, 11), relates to an element 38 which occludes a vessel distal to the catheter 18 or, at least, distal to the mechanical and pharmacologic segments 26 of the catheter 18. This occluding element 38 can take any one of several forms, including an inflatable balloon (not shown), a deformable mesh braid 45 with a membrane 41, a malecot with a membrane (not shown), or other suitable configuration. A preferred embodiment (FIGS. 8, 9) consists of a deformable mesh braid 45 mounted on the outer surface 43 of a movable core guide wire 20. When the inner core 42 is retracted 44 in relation to the outer surface 43 (FIG. 9), the braid 45 changes from a longitudinal tubular structure (FIG. 8) to a radially expanded disc like structure (FIG. 9) which occludes the lumen of the vessel. The membrane 41 covers or is disposed in the interstices 46 of the braid 45. The wire 20 is preferentially inserted through the catheter 18 and may or may not be designed so as to assist in the motions of the catheter 18 described above. A primary purpose of this element 38 is to keep the pharmacologically active thrombolytic drug from washing out of the area of the clot 1 once some of the clot 1 has been dissolved. The prior art infusion catheters frequently are effective in restoring a channel within the clot, but subsequently the thrombolytic drug is washed away from the clot secondary to the success of re-establishing flow. Further thrombolysis is the result of a systemic effect of the drug, rather than the desired local drug delivery of the infusion catheter. This situation necessitates longer infusion times utilizing more expensive thrombolytic drugs. This translates into added costs to achieve complete thrombolysis. The occluding element 38 of the current invention would prevent the washout of the thrombolytic drug from the thrombus, accelerating the thrombolytic process. Protection against embolization is a secondary purpose.

Balloons have been used for greater than 30 years to temporarily occlude vessels. Filters are included in more recent prior art to protect against distal embolization, but the occluding device of the current invention, in the form of a malecot or deformable mesh braid 45 containing a more or less impermeable elastomeric membrane 41, has not been utilized before.

Therefore, the foregoing description details a unique device and method that creates time and cost efficiencies in removing thrombus from the vascular channels of the human body. The device differs from prior art in addition to those previously listed features, in: 1) the length of the mechanically active segment 26, 2) the distribution of the apertures 10 for drug insertion when combined with a mechanically active segment 26, 3) the configuration and programmability 15 of the motor drive 14, 4) the presence of a motor controller 13, 5) the distal occluding element 38, 6) need to move the mechanically active segment 26 within the clot (prior art), and 7) the inclusion of a combination of these features within one device. The device and method of the current invention also differs from prior art in that it expedites long segment thrombolysis, something that has never been achieved with prior art devices. The present invention provides for a short interventional procedure to place the device, begin infusion and initiate desired mechanical action. When the patient returns in one to several hours, the thrombolytic process is complete, the device can then be removed, and patient discharged shortly thereafter.

The present invention is preferably used to clear long segment occlusions secondary to thrombus within arteries, veins, and grafts. In the case of iliofemoral deep venous thrombosis (clot involving the iliac, superficial femoral, and popliteal veins), a preferred procedure is to percutaneously enter the popliteal vein via a Seldinger approach, insert a multipurpose angiographic catheter, and inject a small amount of contrast medium centrally. This will determine the extent of the thrombus in the iliac vein. The initial catheter is then exchanged for the device of the current invention that is positioned so that the mechanically active segment 26, and the aperture containing segment 25, span the entire length of the clot. The lengths of these segments are chosen from one of several different models of the device so that the length of the active segments 26 matches the length of clot 1 within the patient. If desired the distal occlusion element 38 may be deployed at this time, or even before the catheter device 18 of the invention is inserted. The mechanical portion 26 of the catheter 18 is connected to the drive motor 14, and the infusion lumen 28 is connected to the drug infusion pump 12. Appropriate desired frequencies, actions, motions, pauses, etc., are programmed 15 into the drive motor controller 13, and the motor 14 initiated. The flow rate of the thrombolytic drug is selected and the drug infusion pump 12 is begun. The patient is then transferred to a holding area, hospital room, or critical care unit for observation. The thrombolysis may be monitored by duplex compression ultrasound, but eventually the patient will return to the interventional suite to be evaluated with contrast injection, usually within three to five hours.

In the case of superficial femoral artery thrombosis or femoropopliteal bypass graft occlusion from thrombus, either the ipsilateral femoral artery or contralateral femoral artery may be entered by Seldinger technique. A contrast agent is injected to determine the extent of the clot, and the appropriate device 18 of the invention is chosen to match the length of clot within the patient. It is positioned, with or without the distal occlusion device 38, so that the mechanically active 26 and pharmacologically active 25 segments essentially span the entire clot 1. The connections are made as above, and the appropriate parameters chosen and programmed 15. The mechanical segment 26 and the pharmacological segment 26 are initiated. The patient is then handled as in the prior paragraph. An endpoint is reached when pulses are detected clinically, or when the patient is returned to the angiography suite to be restudied. Any residual debris within the vessel may be aspirated before removing the distal occlusion device 38.

In addition to the description and guidance provided herein, the present inventor provides additional written description and enablement support for the present invention by incorporation by reference of U.S. Pat. Nos. 5,279,546 and 5,569,275.

It is obvious that variations of these methods may be employed to achieve the same desired effect. It is understood that various modifications of the device of the current invention and method may be accomplished within the scope of this invention.

What is claimed is:

1. A pharmomechanical device, comprising:
   a catheter having a corkscrew configuration throughout its length that is substantially incapable of damaging an endothelium of a vascular structure, said catheter rotating between 30 rpm and 600 rpm once it is inserted inside a patient, said catheter increasing the surface area of a clot in said vascular structure such that said clot can be dissolved by a lytic agent; and
   means for providing mechanical motion to said catheter throughout a length of a vessel for a prolonged period of time while said lytic agent is acting.

2. The device as set forth in claim 1, wherein said period is at least about 5 hours.

3. The device as set forth in claim 1, wherein said period is at least about 10 hours.

4. The device as set forth in claim 1, wherein said period is at least about 24 hours.

5. The device as set forth in claim 1, wherein said means for providing mechanical motion operates intermittently and over a prolonged period of time.

6. The device as set forth in claim 5, wherein said means for providing mechanical motion provides for a time of inactivity at least as great as a time of activity of said device.

7. The device as set forth in claim 1, wherein said means for providing mechanical motion generates vibrations effective to disrupt a clot, but does not promote hemolysis or cause damage to an endothelium.

8. The device as set forth in claim 1, wherein said corkscrew configured catheter extends for a substantial length of said vessel.

9. The device as set forth in claim 1, further comprising an occluding element positioned so as to maintain desired concentration of a thrombolytic drug in a desired segment of a patient's blood vessels.

10. The device as set forth in claim 6, wherein a ratio of an inactivation time to an activation time is greater than 1.

11. The device as set forth in claim 6, wherein a ratio of an inactivation time to an activation time is greater than 50.

12. The device as set forth in claim 1, further comprising a pump that delivers lytic agent in pulse waves, said pulse waves causing an intermittent mechanical motion of said catheter, and wherein an intermittent mechanical motion of the catheter is caused by the delivery of said lytic agent.

13. The device as set forth in claim 12, wherein said pump is programmed to deliver said lytic agent at a desired frequency or duration.

14. A pharmomechanical device, comprising:
   a catheter having a length and having a corkscrew configuration throughout a substantial portion of said length, said catheter being substantially incapable of damaging an endothelium of a vascular structure, said catheter rotating between 30 rpm and 600 rpm once it is inserted inside a patient to increase the surface area of a clot in said vascular structure; and
   a means for rotating said catheter.

15. The pharmomechanical device of claim 14, wherein said catheter rotates at less than about 300 rpm.

16. The pharmomechanical device of claim 14, wherein said catheter rotates at less than about 55 rpm.

17. A pharmomechanical device, comprising:
   a catheter having a corkscrew configuration throughout substantially its entire length that is substantially incapable of damaging an endothelium of a vascular structure, said catheter rotating less than about 55 rpm once it is inserted inside a patient, said catheter increasing the surface area of a clot in said vascular structure such that said clot can be dissolved by a lytic agent; and
   a pump that delivers lytic agent in pulse waves, said pulse waves causing an intermittent mechanical motion of said catheter.

* * * * *